(12) United States Patent
Chen et al.

(10) Patent No.: US 8,367,010 B2
(45) Date of Patent: Feb. 5, 2013

(54) OZONE DEVICE FOR DEODORIZING DRESSES

(75) Inventors: Chung-Yang Mike Chen, Irvine, CA (US); Robert Desantis, Beverly Hills, CA (US)

(73) Assignee: Chung-Yang Mike Chen, Irvine, CA (US)

( * ) Notice: Subject to any disclaimer, the term of this patent is extended or adjusted under 35 U.S.C. 154(b) by 539 days.

(21) Appl. No.: 12/703,851

(22) Filed: Feb. 11, 2010

(65) Prior Publication Data

US 2011/0194981 A1    Aug. 11, 2011

(51) Int. Cl.
  *B01J 19/08* (2006.01)
  *A61L 9/00* (2006.01)
  *C01B 13/10* (2006.01)
  *A61M 37/00* (2006.01)
  *A61M 15/02* (2006.01)

(52) U.S. Cl. .............. 422/305; 422/186.12; 422/186.07; 422/292; 204/176; 604/23; 604/25; 128/202.25

(58) Field of Classification Search ............. 422/186.12, 422/186.07, 292, 305; 204/176; 604/23, 604/25; 128/202.25; 424/613
See application file for complete search history.

(56) References Cited

U.S. PATENT DOCUMENTS

2008/0118411 A1 *  5/2008  D'Arinzo ................ 422/186.09

\* cited by examiner

*Primary Examiner* — Jill Warden
*Assistant Examiner* — Monzer Chorbaji
(74) *Attorney, Agent, or Firm* — Rosenberg, Klein & Lee (57) ABSTRACT

An ozone device for deodorizing dresses within a closet, includes an ozone generator. The ozone generator includes a casing formed with first and second ventilation vents, an ozone producing element installed within the casing for generating ozone in order to deodorizing dresses within the closet, a circulating fan installed within the casing for circulating ozone generated by the ozone producing element, and a hanging unit projecting outward from the casing and adapted to be hung onto a suspension member. The closet is sleeved over and cooperates with the casing to define a sealed chamber so that dresses can be kept therein.

11 Claims, 7 Drawing Sheets

OZONE DEVICE FOR DEODORIZING DRESSES

BACKGROUND OF THE INVENTION

1. Field of the Invention

The present invention relates to an ozone device, more particularly to an ozone device that is adapted to be hung onto a suspension member.

2. Description of the Prior Art

Some dresses of high cost or value (such as silk, leather, feather dresses and furs) are generally sent to laundry for dry cleaning to prevent damage done onto them. However, it is noted that the dry cleaning fee is relatively high and therefore incurs an extra burden for every person or family.

The dresses or uniforms we generally wear in work or offices are usually contaminated with peculiar smell (unwanted smell), thereby causing discomfort to the wearers. For instance, the dress of a smoker is contaminated with cigarette smell that seldom disperses off and the smell is unbearable for those nearby persons. In the event, high-cost dresses worn by the persons accustomed to smoking are always sent to laundry for dry cleaning, there may occur a great extra expense.

A general method for getting rid of the undesired smell is to dispose a smell remover (including drying agent, desiccating agent, an exsiccator, Silica Gel and desiccant) within a clothes wardrobe or cabinet, where the dresses are deodorized by the smell remover. However, since each wardrobe has a considerable space and a relatively large quantity of smell removers must be disposed therein so as to deodorize specific suits of dresses, thereby causing extra expense for purchasing new sets of the smell remover. In addition, majority of the wardrobes have no sealed chamber to prevent leakage of the deodorizing effect, the deodorizing effect produced by the smell remover is decreased due to presence of the gap, which, in turn, causes the user to purchase a new set of smell remover at a predetermined short period of time. In case other electronic deodorizing device, which is relatively expensive when compared to the smell remover, is disposed within the wardrobe to deodorize the dresses, an extra expense will be caused to the user and therefore using electronic deodorizing device is not economized.

SUMMARY OF THE INVENTION

Therefore, in order to solve the above-mentioned drawbacks, it is the object of the present invention is to provide an ozone device of a hanging type. The ozone device includes an ozone generator and a closet enclosing the ozone generator in such a manner to define a sealed chamber for keeping the dresses therein. Thus, the ozone generated from the ozone generator deodorizes the dresses in an effective way due to being confined within the sealed chamber and due to sealed proof of the sealed chamber, thereby causing the ozone generator to produce lesser amount of ozone and reducing the risk happened due to leakage of ozone from the sealed chamber.

An ozone device is provided according to the present invention for deodorizing dresses within a closet, includes an ozone generator and the closet. The ozone generator includes a casing formed with first and second ventilation vents, an ozone producing element installed within the casing for generating ozone in order to deodorizing dresses within the closet, a circulating fan installed within the casing for circulating ozone generated by the ozone producing element, and a hanging unit projecting outward from the casing and adapted to be hung onto a suspension member. The closet is sleeved over and cooperates with the casing to define a sealed chamber so that dresses can be kept therein.

The ozone device of the present invention further includes a control module for controlling activating and de-activating the ozone producing element and the circulating fan, and a switch for generating and transmitting an activating signal to the control module in such a manner that the control module activates the ozone producing element and the circulating fan upon receipt of the activating signal from the switch and de-activates the ozone producing element after a first preset time.

When the circulating fan is activated, the ozone generated by the ozone producing element enters into the sealed chamber via the first ventilation rent and returns back into the casing via the second ventilation vent.

The control module deactivates the circulating fan after a second preset time elapsed. The second preset time is longer than the first preset time.

As explained above, since the casing and the closet in the present ozone device cooperatively define the sealed chamber to prevent leakage of ozone therefrom, the dresses kept therein are deodorized by the ozone. In other words, only a small amount of ozone is required to circulate within the closet in order to deodorize the dresses, in addition to economizing the electrical power for operation of the ozone producing element. Thus, the battery unit installed within the ozone device of the present invention lasts longer when compared to prior ones. Due to presence of the control module within the closet and since the control module deactivates the ozone producing element after a short period of time and the circulating fan after a longer period of time, the dresses kept within the closet are deodorized effectively. When compared to prior ones, the ozone device of the present invention consumes lesser electrical power, thereby economizing a large amount of electrical power.

In addition, since the ozone generated by the ozone producing element is confined within the sealed chamber and is prevented from leaking to exterior of the closet, the health of nearby persons is exposed to the lowest danger.

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENTS

Figure 1:
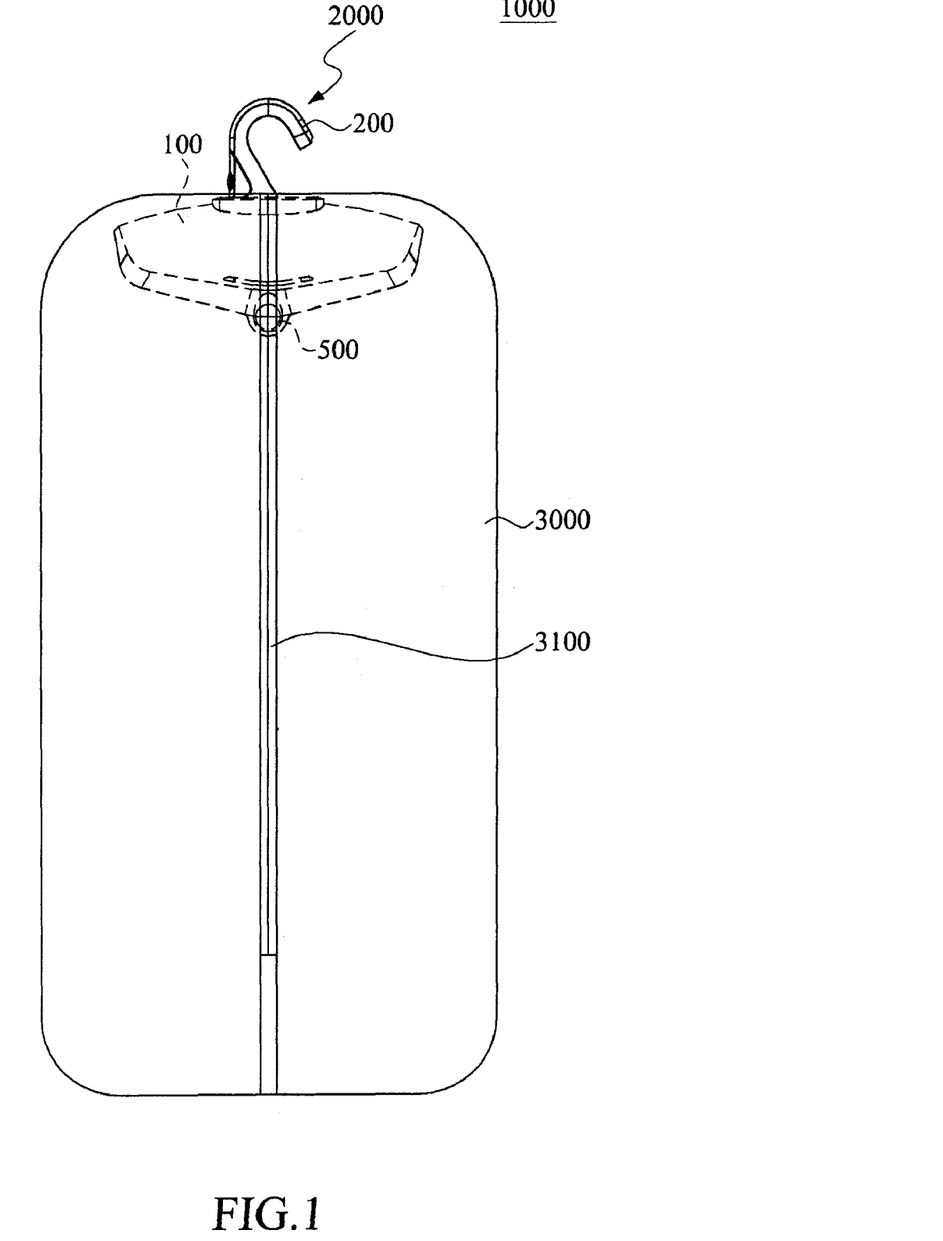
FIG. 1 is a schematic view of the first embodiment of an ozone device of the present invention.

FIG. 1 is a schematic view of the first embodiment of an ozone device of the present invention. As illustrated, the ozone device 1000 accordingly includes an ozone generator 2000 and a closet 3000 (including garment bag, wardrobe, showcase, sleeve and box). The ozone generator 2000 is capable of generating ozone while the closet 3000 is sleeved over and cooperates with the casing 100 to define a sealed chamber so that dresses can be kept therein.

Figure 5:
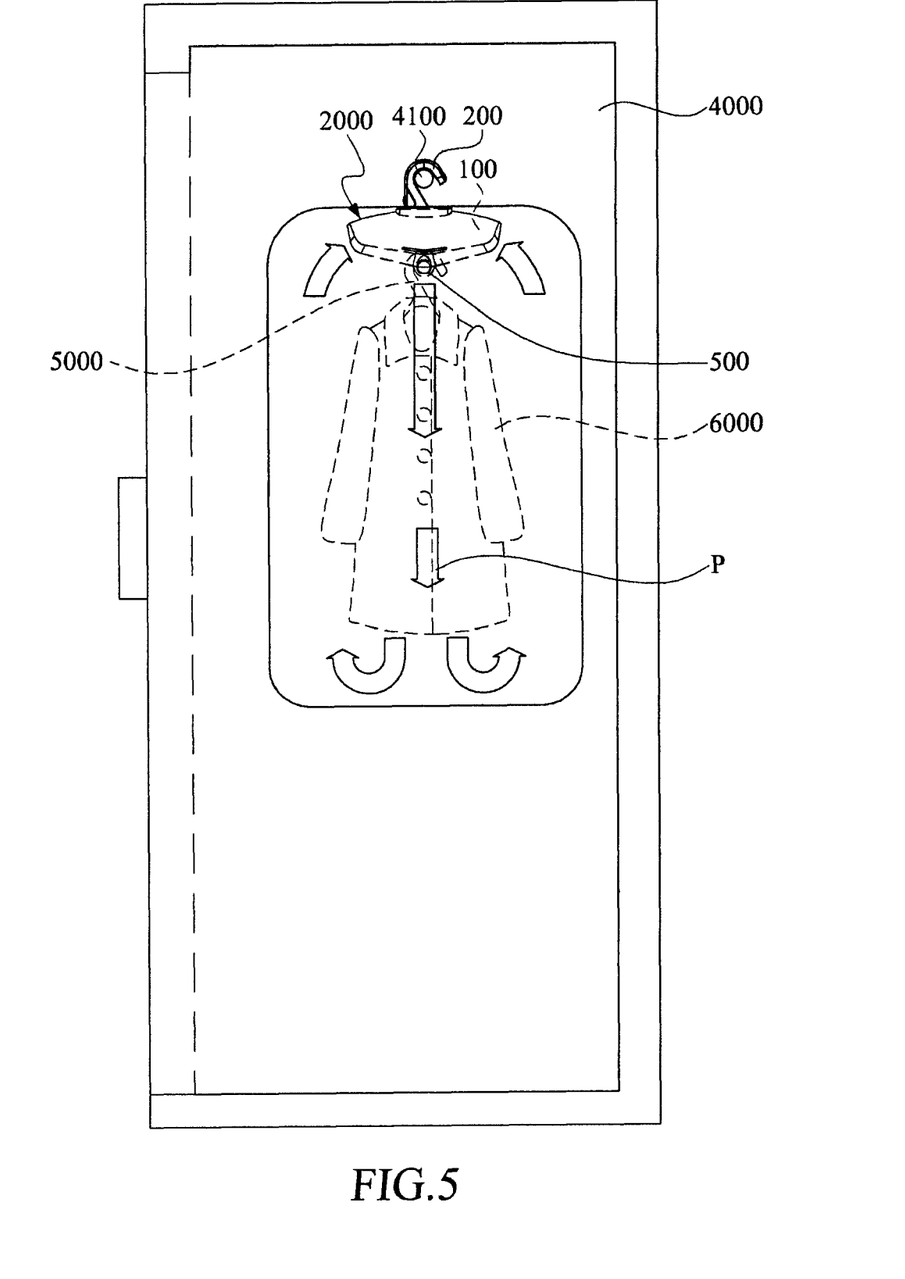
FIG. 5 illustrates how the ozone device of the present invention is used within a wardrobe.

The closet 3000 further includes a zipper 3100 for fastening an opening for access into the sealed chamber. The ozone generator 2000 includes a casing 100 for disposing within the closet or wardrobe 3000, a hanging unit 200 and a suspending rod unit 500. The zipper 3100 is pulled downward to uncover the opening via which the ozone generator 2000 can be inserted into the closet 3000 such that the hanging unit 200 projecting outward from a top portion of the closet 3000 and is adapted to be hung onto a suspension member (as shown in FIG. 5). Under this condition, the closet 3000 and the casing 100 do not separate and cooperatively define the sealed chamber.

Figure 2:
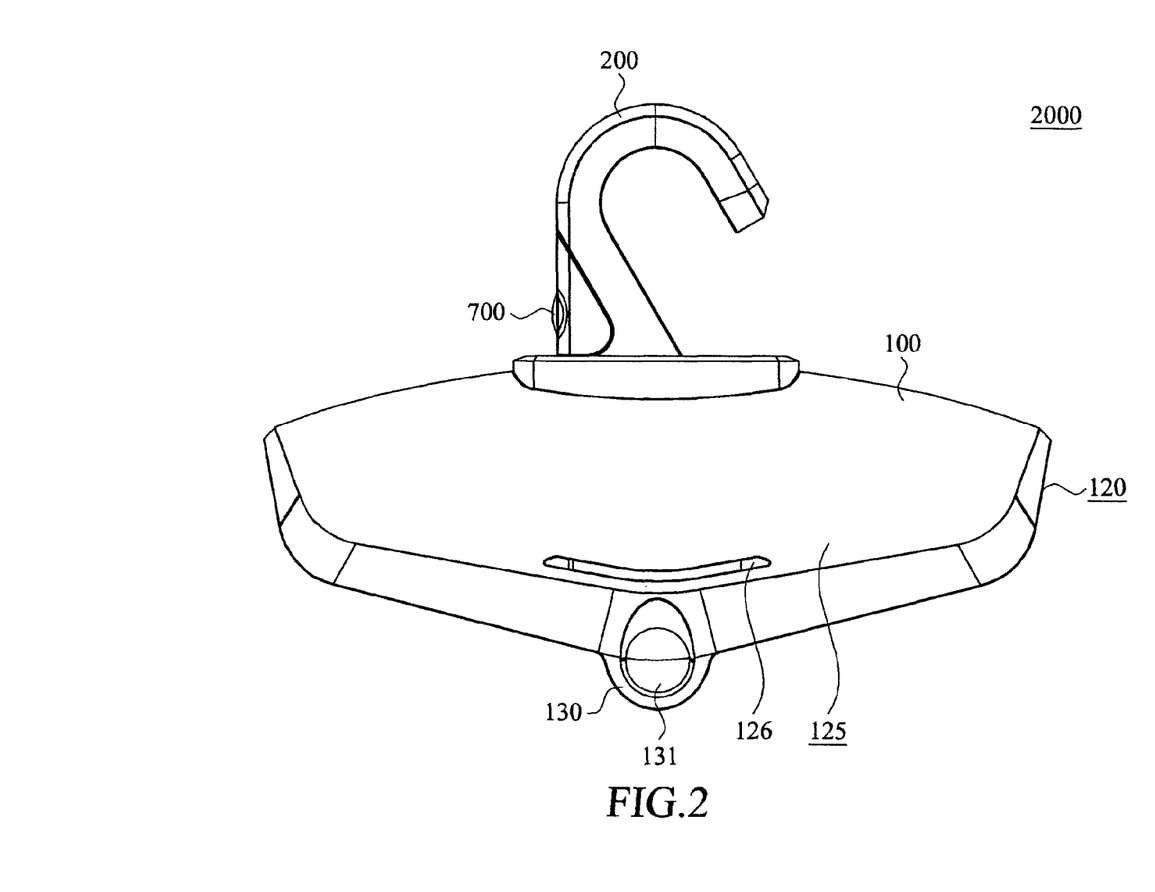
FIG. 2 shows an ozone generator employed in the ozone device of the present invention.
Figure 3:
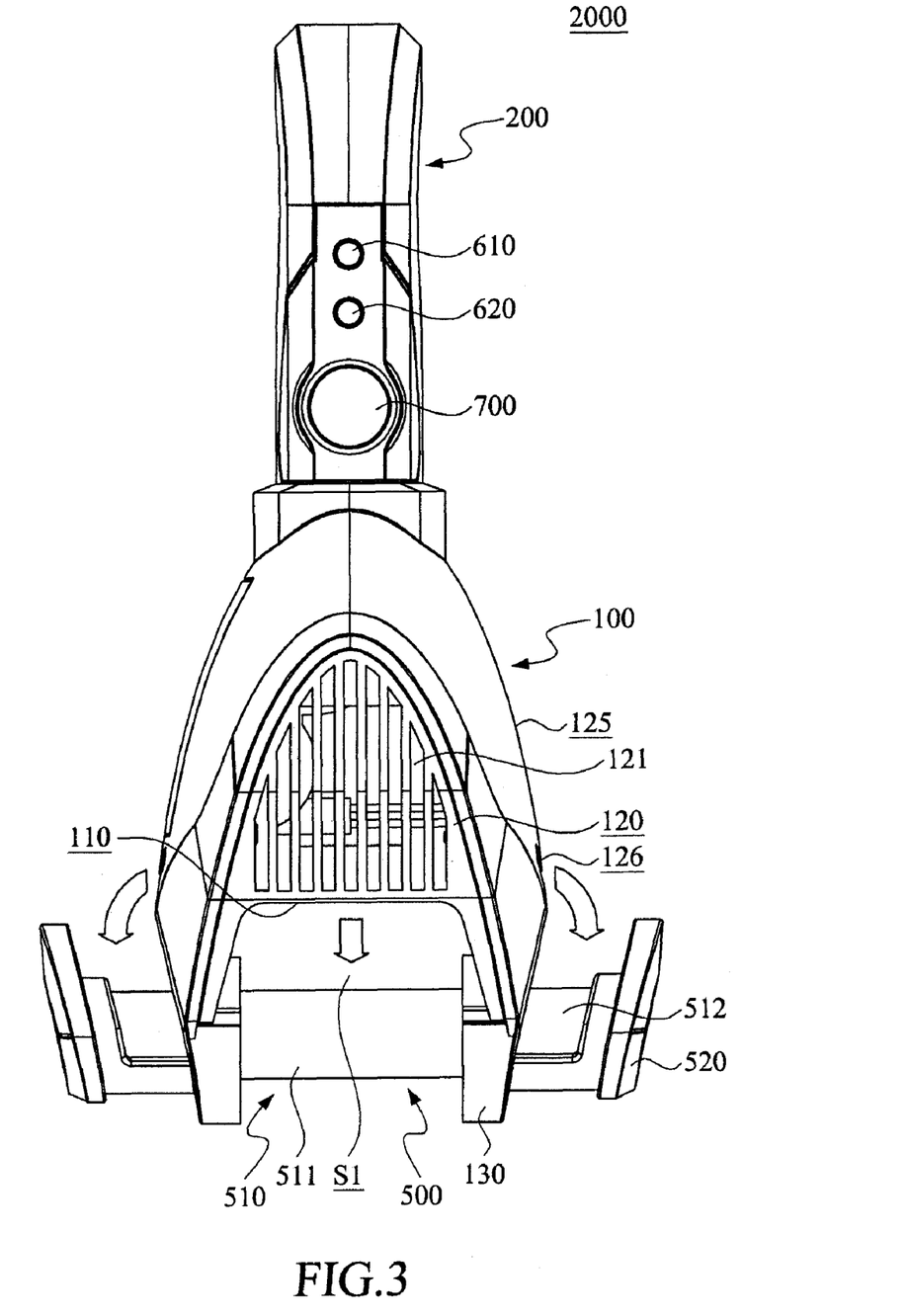
FIG. 3 is a lateral side view of the ozone generator employed in the ozone device of the present invention.
Figure 4:
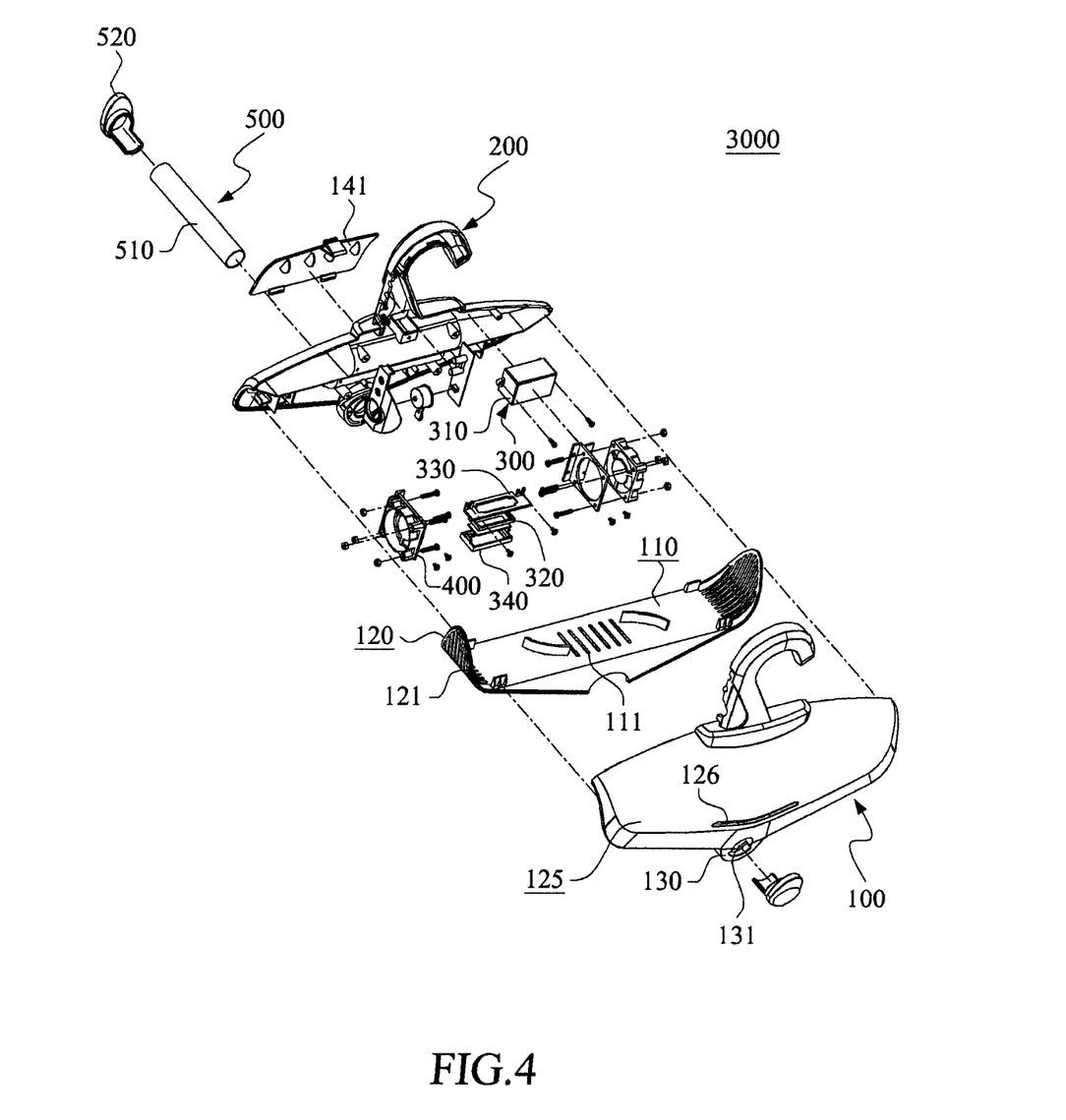
FIG. 4 is an exploded view of the ozone generator shown in FIG. 2.
Figure 4A:
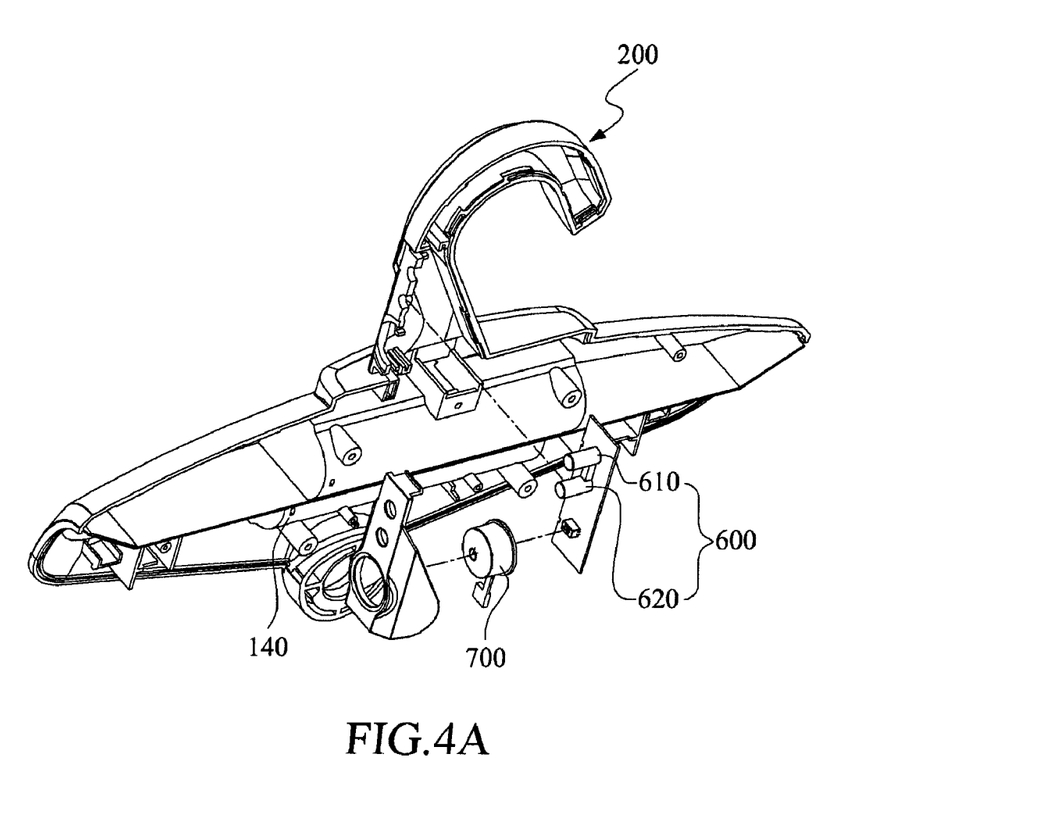
FIG. 4A is a partly exploded view of the ozone generator shown in FIG. 2.

Referring to FIGS. 2 to 4, wherein FIG. 2 shows the ozone generator 2000 employed in the ozone device 1000 of the present invention, FIG. 3 is a lateral side view of the ozone generator 2000 employed in the ozone device 1000 of the present invention, FIG. 4 is an exploded view of the ozone generator 2000 shown in FIG. 2 while FIG. 4A is a partly exploded view of the ozone generator 2000 shown in FIG. 2. As shown, the ozone generator 2000 further includes an ozone producing element 300, two circulating fans 400, a suspending rod unit 500, a control module 600 and a switch 700.

In this embodiment, the casing 100 has one bottom wall 110, front and rear walls 120, and left and right walls 125. The bottom wall 110 is formed with a first ventilation vent 111. Each of front and rear walls 120 is formed with a second ventilation vent 121 while each of the left and right walls 125 is formed with a third ventilation vent 126.

The hanging unit 200, in fact a hook member, is integrally formed with and projects upwardly from the casing 100 and is adapted to be hung detachably onto a suspension member (a rail 4100 within a wardrobe shown in FIG. 5).

The ozone producing element 300 is installed within the casing 100 for generating ozone in order to deodorizing dresses within the closet 3000. In addition to the dresses, consumer items likes shoes and hats, can kept within the closet 3000 for drying purpose if desired. The ozone producing element 300 includes an ozone emitter 320, an ozone controller 310 electrically coupled with the ozone emitter 320, upper and lower protection covers 330, 340. The ozone controller 310 controls supply of electrical power to the ozone emitter 320. The ozone emitter 320 can be a ceramic plate enclosed by the upper and lower protection covers 330, 340. Since controlling of the ozone controller 310 relative to the ozone emitter 320 is a known art, a detailed description thereof is omitted herein for brevity.

The circulating fans 400 are installed within the casing 100, at two opposite sides of the ozone emitter 320 respectively adjacent to the second ventilation vents 121. In this embodiment, the blow direction of the fans 400 is directed toward the ozone emitter 320 such that the ozone within the casing 100 passes through the first and third ventilation vents 111, 126 and enters into the closet 3000. Later, the ozone within the closet 3000 enters into the casing 100 via the second ventilation vents 121. Alternately, the circulating fans 400 can be disposed exterior to the casing 100, respectively adjacent to the first and second ventilation vents 111, 121.

Location of the first, second and third ventilation vents 111, 121, 126 on the casing 100 should not be limited to a specific spot. Any position is possible so long as to permit smooth flow of ozone from the casing 100 into the closet 3000 and vice versa. For instance, the first ventilation vent 111 is formed through the bottom wall while the second ventilation vents 121 are formed through the lateral side walls of the casing 100. The blown direction of the fans 400 is not restricted to any specific direction so long as the air circulates smoothly within the closet 3000 will be alright.

The suspending rod unit 500 is fixed to the casing 100, includes a clothe hanger 5000 hung detachably onto the suspension member for carrying the dresses 6000 thereon (see FIG. 5). The suspending rod unit 500 includes an inner suspending rod 510 and two outer suspending rods 520 attached respectively to opposite ends of the inner suspending rod 510.

The casing 100 further has a suspension lug 130 that projects downward from the bottom wall 110 and that is formed with a rod hole 131 for extension of the inner suspending rod 510 when the suspending rod unit 500 is mounted to the lug member 130. Under this condition, the inner suspending rod 510 is disposed below and cooperates with the bottom wall 110 of the casing 10 to define a gap S1 to facilitate passage of the clothe hanger 5000 therethrough and the inner suspending rod 510 itself defines an inner hanging room 511 while the outer suspending rods 520 are disposed exterior to the lug member 130 to define two outer hanging rooms 512. As illustrated in FIG. 3, in case the clothe hanger 5000 is hung onto the inner or outer hanging room 511, 512, the dresses carried by the hanger 5000 will be deodorized by the ozone emitted from the first ventilation vent 111 while the dresses carried by another clothe hanger on the outer hanging room 512 will be deodorized by the ozone emitted from the third ventilation vents 126. Since the undesired smell is generally contaminated on the external surface of the dresses, and the dresses being exposed to the first and second ventilation vents 111, 121 will be deodorized effectively.

Referring to FIG. 4A, the control module 600 is disposed within the casing 100 for activating and de-activating the ozone producing element 300 and the circulating fans 400. The control module 600 preferably includes an ozone indicating lamp 610 and a power indicating lamp 620, each consisting of several LEDs (Light Emitting Diode). It is preferred to arrange the lamps 610, 620 to have different colors. When the ozone producing element 300 is under operation, the lamp 610 will be switched ON and when the ozone producing element 300 is not in operation, the lamp 610 will be switched OFF or emits light intermittently. When the ozone producing element 300 and the fans 400 are activated, the power lamp 620 will be switched On. Switch-off state of the power lamp 620 indicates the ozone producing element 300 and the fans 400 are not in operation.

The switch 700 is installed within the casing 100, and is coupled electrically with the control module 600. The switch 700 is used for transmitting an activating signal to the control module 600 such that the ozone producing element 300 and the circulating fans 400 are simultaneously activated upon receipt of the activating signal from the switch 700 and that the ozone producing element 300 is deactivated after a first preset time elapsed. In other words, the control module 600 deactivates the circulating fans 400 after a second preset time that is greater than the first preset time. For instance the first preset time is 10 minutes while the second preset time is 60 minutes. The lamp 610 will be switched ON during the first preset time, i.e., the ozone producing element 300 is under operation and generating ozone. The power lamp 620 may emit green light, denoting the ozone producing element 300 and the fans 400 are under operation. After the first preset time has elapsed and during the second preset time, the ozone producing element 300 and the fans 400 can be deactivated, but the ozone lamp 610 may emit light intermittently with the power lamp 620 being switched OFF. Under such condition, the user is reminded not to open the closet 3000 due to presence of ozone gas therein. After the second preset time has elapsed and in the event the ozone lamp 610 and the power lamp 620 are switched OFF, which means that is safe to open the closet 3000 for fetching out the dresses.

In another embodiment, during the first preset time, the ozone lamp 610 can be arranged to emit red rays. This means that the ozone producing element 300 and the fans 400 are in the operation mode. The second preset time can be 20 minutes so that during the second preset time, the ozone lamp 610 may emit red rays intermittently while the power lamp 620 emits green light rays. It is to understand that the fan 400 is in the operation mode due to remaining ozone within the closet 3000. Alternately, a third preset time can be arranged after the second preset time. The third preset time can be 60 minutes, where the ozone lamp 610 may emit red rays intermittently while the power lamp 620 is switched OFF. It is to understand that there is remaining ozone in the closet 3000; the user is warned not to open the closet 3000 so as to prevent leakage of the remaining ozone to the exterior of the closet 3000.

Since the zone generated by the ozone producing element 300 circulates within the sealed chamber 3000 along a circulation path and since the control module 600 can adjust activation of the ozone producing element 300 and the fan 400, a relatively large amount of electrical power can be economized.

The casing 100 further includes a battery chamber 140 for receiving a battery unit therein, which supplies electrical power to the ozone producing element 300, the circulating fan 400 and the control module 600. A lid 141 is detachably mounted on the chamber 140 for covering the battery unit.

FIG. 5 illustrates how the ozone device 1000 of the present invention is used within a wardrobe or cabinet. Also referring to FIGS. 4 and 4A, the wardrobe 400 is provided with a suspension member 4100, upon which the hanging unit 200 can be detachably hooked on. Under this condition, the clothe hanger 5000 with the dresses 6000 can be hooked detachably onto the suspension rod unit 500. Since the closet 3000 being sleeved over the ozone generator 2000 and when the circulating fans 400 are activated, the ozone from the casing 100 is outputted into the closet 3000 via the first and third ventilation vents 111, 126 so as to deodorize the smell stained on external surfaces of the dresses 6000 when the ozone flows along the circulation path P. Later, the ozone flows back into the casing 100 via the second ventilation vents 121. In another embodiment, the dresses 6000 can be hooked directly and detachably on the suspension rod unit 500.

Figure 6:
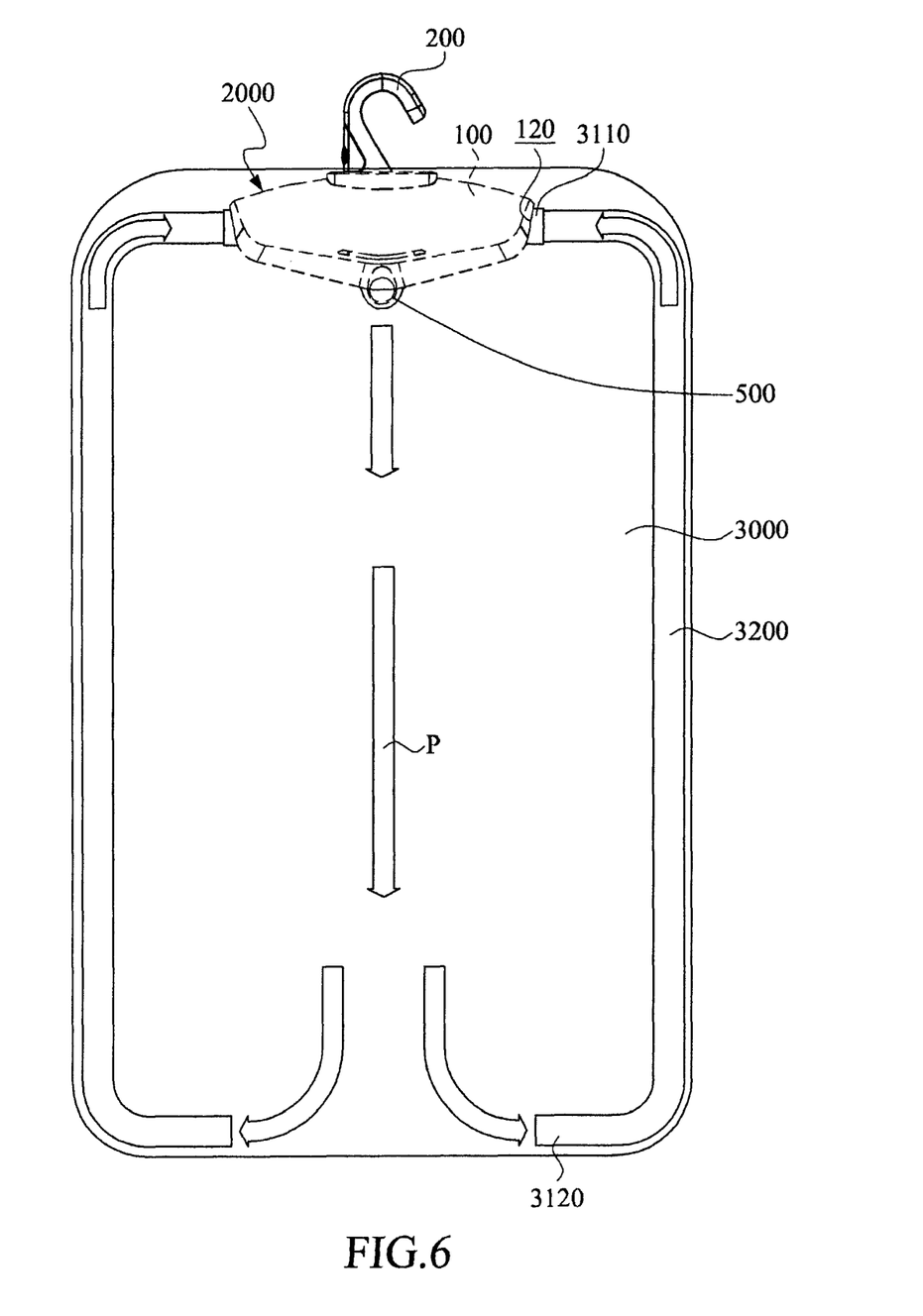
FIG. 6 is a schematic view of the second embodiment of an ozone device of the present invention.

FIG. 6 is a schematic view of the second embodiment of an ozone device of the present invention. Also referring to FIGS. 4 and 4A, the second embodiment has the similar structure as the first embodiment depicted in FIG. 2. The only difference resides in that the closet 3000 further includes a fluid tube 3200 having a first end 3110 connected fluidly to a respective second ventilation vent 121 on the wall 120 and a second end 3120 terminating at a lower portion of the closet 3000. Alternately, one end of the fluid tube 3200 can be connected fluidly to the first or third ventilation vent 111, 126. The restriction should not be limited only thereto.

In the second embodiment shown in FIG. 6, upon activation of the circulating fan 400, the ozone from the casing 100 is outputted into the closet 3000 via the first and third ventilation vents 111, 126 when the ozone flows along the circulation path P without passing through the second ventilation vents 121. Later, the ozone flows back into the casing 100 via the second end 3120 of the fluid tube 3200 and the first end 3110 connected fluidly to the respective second ventilation vent 121 on the wall 120. Since the ozone generated by the ozone generator 2000 is confined within the sealed chamber defined cooperatively by the closet 3000 and the casing 100 and circulates within the sealed chamber repeatedly, the ozone stays within the closet 3000 for a relatively long time. The control module 600 is arranged to control the ozone generator 2000 to operate for short period of time, but the circulating fan 400 for a longer period of time to circulate the ozone for a relatively long time to deodorize the dress. Thus, the ozone device 1000 of the present invention consumers lesser power source when compared to the prior art ones.

In addition, since the present ozone device generates lesser ozone amount when compared to the prior art ones and the amount is confined within the closet 3000 and being prevented from leaking to exterior of the closet, there is no danger caused the health of nearby persons.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An ozone device for deodorizing dresses, comprising:
 an ozone generator including
  a casing formed with first and second ventilation vents;
  an ozone producing element installed within said casing for generating ozone in order to deodorizing dresses;
  a circulating fan installed within said casing for circulating ozone generated by said ozone producing element; a suspending rod unit fixed to said casing; a clothes hanger hung detachably over said suspending rod unit for carrying the dresses thereon, said suspending rod unit includes an inner suspending rod, which is mounted within said casing, and over which said clothe hanger is hung detachably; and
  a hanging unit projecting outward from said casing and adapted to be hung onto a suspension member; and
 a closet being sleeved over and cooperating with said casing to define a sealed chamber so that dresses can be kept therein said closet further including a zipper for fastening an opening for access into the sealed chamber.

2. The ozone device according to claim 1, wherein said casing has a bottom side formed with said first ventilation vent and a lateral side formed with said second ventilation vent.

3. The ozone device according to claim 1, wherein said casing has a bottom side formed with said second ventilation vent and a lateral side formed with said first ventilation vent.

4. The ozone device according to claim 1, wherein said ozone generated by said ozone producing element circulates along a circulation path within said closet.

5. The ozone device according to claim 1, wherein said casing further has a suspension lug member that projects downward from a bottom side thereof and that is formed with a rod hole for extension of said inner suspending rod when said suspending rod unit is fixed to said casing.

6. The ozone device according to claim 5, wherein said suspending rod unit further includes an outer suspending rod projecting outward from said suspension lug member of said casing.

7. The ozone device according to claim 1, further comprising
 a control module for controlling activating and de-activating said ozone producing element and said circulating fan, and a switch for generating and transmitting an activating signal to said control module, wherein, said control module activates said ozone producing element and said circulating fan upon receipt of said activating signal from said switch and deactivates said ozone producing element after a first preset time elapsed.

8. The ozone device according to claim 7, wherein said control module deactivates said circulating fan after a second preset time elapsed, said second preset time being greater than said first preset time.

9. The ozone device according to claim 1, wherein said ozone producing element further includes an ozone emitter for producing said ozone, and, an ozone controller for controlling supply of electrical power to said ozone emitter in order to produce said ozone.

10. The ozone device according to claim 9, wherein said ozone generator includes two pieces of said circulating fan respectively disposed at two opposite sides of said ozone producing element.

11. The ozone device according to claim 1, wherein said casing further includes a battery chamber for receiving a battery unit therein, which supplies electrical power to said ozone producing element and said circulating fan.

* * * * *